(12) United States Patent
Chen et al.

(10) Patent No.: US 12,167,891 B2
(45) Date of Patent: *Dec. 17, 2024

(54) HANDHELD OPHTHALMIC LASER SYSTEM WITH REPLACEABLE CONTACT TIPS AND TREATMENT GUIDE

(71) Applicant: IRIDEX Corporation, Mountain View, CA (US)

(72) Inventors: Howard Chen, San Jose, CA (US); David Buzawa, San Jose, CA (US)

(73) Assignee: Iridex Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,291

(22) Filed: Jan. 12, 2023

(65) Prior Publication Data

US 2023/0141548 A1    May 11, 2023

Related U.S. Application Data

(60) Continuation of application No. 16/938,030, filed on Jul. 24, 2020, now Pat. No. 11,576,569, which is a
(Continued)

(51) Int. Cl.
*A61B 3/00* (2006.01)
*A61B 18/22* (2006.01)
(Continued)

(52) U.S. Cl.
CPC ............ *A61B 3/0008* (2013.01); *A61B 18/22* (2013.01); *A61F 9/00821* (2013.01);
(Continued)

(58) Field of Classification Search
CPC ....... A61B 3/0008; A61B 18/22; A61B 18/18; A61F 9/00821; A61F 2009/00868; A61F 2009/00891; B23K 26/0096; B23K 26/02
See application file for complete search history.

(56) References Cited

U.S. PATENT DOCUMENTS 5,121,740 A    6/1992    Uram
5,151,098 A    9/1992    Loertscher
(Continued)

FOREIGN PATENT DOCUMENTS

CN    201085686 Y    7/2008
CN    101309725 A    11/2008
(Continued)

OTHER PUBLICATIONS

"G-Probe™ Operator Manual", Iridex, 131 05-EN Rev D, May 2013, 17 pages.
(Continued)

*Primary Examiner* — Shirley X Jian
(74) *Attorney, Agent, or Firm* — Kilpatrick Townsend & Stockton LLP

(57) ABSTRACT

In some embodiments, an ophthalmic laser system may be provided that does not include a traditional laser console. Instead, the treatment device may be configured to house the treatment light source within the device handle. Additionally, in some embodiments, the handheld treatment device may include a user interface, such as dials and buttons, for adjusting various parameters of the therapeutic light. With certain embodiments, the self-contained handheld treatment device may be operated independent of an AC power source. For example, in some embodiments, the handheld treatment device may be battery powered. Additionally, the handheld treatment device may be disposable or may utilize replaceable distal tips in certain embodiments. Certain embodiments may be particularly designed for transscleral cyclophotocoagulation. Also, treatment guides are provided that may be configured to couple with a treatment device to align the device with a target tissue of the eye.

18 Claims, 11 Drawing Sheets

Related U.S. Application Data division of application No. 15/638,036, filed on Jun. 29, 2017, now Pat. No. 10,758,118.

(60) Provisional application No. 62/357,012, filed on Jun. 30, 2016.

(51) Int. Cl.
*A61F 9/008* (2006.01)
*B23K 26/00* (2014.01)
*A61B 18/18* (2006.01)
*B23K 26/02* (2014.01)

(52) U.S. Cl.
CPC .......... *B23K 26/0096* (2013.01); *A61B 18/18* (2013.01); *A61F 2009/00868* (2013.01); *A61F 2009/00891* (2013.01); *B23K 26/02* (2013.01)

(56) References Cited

U.S. PATENT DOCUMENTS

| | | | |
|---|---|---|---|
| 5,217,452 A | 6/1993 | O'donnell | |
| 5,372,595 A * | 12/1994 | Gaasterland | A61F 9/008 606/4 |
| 5,460,182 A * | 10/1995 | Goodman | A61B 5/0084 600/478 |
| 5,478,338 A | 12/1995 | Reynard | |
| 5,514,125 A | 5/1996 | Lasser et al. | |
| 5,533,998 A | 7/1996 | Freese et al. | |
| 5,540,678 A * | 7/1996 | Long | A61B 18/22 606/17 |
| 5,549,596 A | 8/1996 | Latina | |
| 5,549,632 A | 8/1996 | Lai | |
| 5,582,608 A * | 12/1996 | Brown | A61B 17/0231 606/4 |
| 5,752,967 A | 5/1998 | Kritzinger et al. | |
| 5,807,380 A | 9/1998 | Dishler | |
| 5,921,981 A * | 7/1999 | Bahmanyar | A61F 9/008 606/4 |
| 5,928,220 A | 7/1999 | Shimoji | |
| 5,968,033 A | 10/1999 | Fuller et al. | |
| 6,013,096 A | 1/2000 | Tucek | |
| 6,059,772 A | 5/2000 | Hsia et al. | |
| 6,221,028 B1 | 4/2001 | Lieberman et al. | |
| 6,319,274 B1 * | 11/2001 | Shadduck | A61N 5/0613 607/90 |
| 6,419,627 B1 * | 7/2002 | Ben Nun | A61F 9/008 606/4 |
| 6,458,120 B1 * | 10/2002 | Shen | A61F 9/00814 606/5 |
| 6,607,524 B1 * | 8/2003 | LaBudde | A61C 1/0046 604/20 |
| 7,277,188 B2 * | 10/2007 | Das | B23K 37/047 356/624 |
| 7,909,040 B2 | 3/2011 | Jones et al. | |
| 7,988,688 B2 * | 8/2011 | Webb | A61N 5/0618 128/898 |
| 8,747,395 B2 | 6/2014 | Rathjen | |
| 8,945,103 B2 * | 2/2015 | Chew | A61F 9/009 606/6 |
| 9,629,749 B2 * | 4/2017 | Vold | A61F 9/008 |
| 9,700,461 B2 | 7/2017 | Buzawa et al. | |
| 10,758,118 B2 * | 9/2020 | Chen | A61F 9/00821 |
| 11,058,890 B2 * | 7/2021 | Chen | A61B 3/14 |
| 11,576,569 B2 * | 2/2023 | Chen | A61B 18/22 |
| 11,771,596 B2 * | 10/2023 | Belkin | A61F 9/0079 606/6 |
| 2002/0126501 A1 | 9/2002 | Toth et al. | |
| 2004/0106081 A1 * | 6/2004 | Karazivan | A61B 5/4547 433/29 |
| 2006/0021623 A1 | 2/2006 | Miller et al. | |
| 2006/0084952 A1 | 4/2006 | Pallikaris et al. | |
| 2006/0095096 A1 * | 5/2006 | DeBenedictis | A61B 90/98 607/88 |
| 2006/0187978 A1 | 8/2006 | Telfair et al. | |
| 2006/0271025 A1 * | 11/2006 | Jones | A61F 9/00802 606/4 |
| 2007/0166049 A1 * | 7/2007 | Pearson | G01H 9/00 398/161 |
| 2008/0097415 A1 | 4/2008 | Zimare et al. | |
| 2008/0107384 A1 | 5/2008 | Nadolski et al. | |
| 2008/0108981 A1 | 5/2008 | Telfair et al. | |
| 2008/0154251 A1 * | 6/2008 | Stuart | A61B 18/203 606/13 |
| 2008/0287935 A1 * | 11/2008 | Bille | A61F 9/00825 606/11 |
| 2009/0021801 A1 * | 1/2009 | Ishihara | G02B 27/48 358/475 |
| 2009/0182312 A1 | 7/2009 | Gertner et al. | |
| 2009/0298391 A1 | 12/2009 | Yamada | |
| 2010/0076419 A1 * | 3/2010 | Chew | A61F 9/00821 606/6 |
| 2010/0130968 A1 | 5/2010 | Vogler | |
| 2010/0202725 A1 * | 8/2010 | Popovich | G02F 1/13731 385/10 |
| 2010/0308968 A1 * | 12/2010 | Tamm | G06K 19/07783 264/400 |
| 2011/0001926 A1 | 1/2011 | Mann et al. | |
| 2011/0069278 A1 | 3/2011 | Gueder | |
| 2011/0112376 A1 * | 5/2011 | Vayser | A61M 1/84 600/249 |
| 2013/0079759 A1 | 3/2013 | Dotson et al. | |
| 2014/0088577 A1 | 3/2014 | Anastassiou et al. | |
| 2014/0142663 A1 | 5/2014 | Van Valen | |
| 2014/0267668 A1 * | 9/2014 | Ignatovich | A61B 3/125 348/78 |
| 2015/0073399 A1 | 3/2015 | Boitor et al. | |
| 2015/0157505 A1 * | 6/2015 | Neev | A61F 9/00814 606/5 |
| 2015/0305938 A1 * | 10/2015 | Vold | A61B 90/30 606/6 |
| 2015/0374539 A1 * | 12/2015 | Buzawa | A61F 9/00781 606/4 |
| 2016/0015565 A1 | 1/2016 | Scheller et al. | |
| 2021/0186755 A1 * | 6/2021 | Khoo | A61F 9/009 |
| 2022/0257416 A1 * | 8/2022 | Foulkes | A61F 9/00736 |

FOREIGN PATENT DOCUMENTS

| | | |
|---|---|---|
| CN | 104936506 A | 9/2015 |
| DE | 19916653 A1 | 10/2000 |
| EP | 0960601 B1 | 10/2006 |
| EP | 2068694 A1 | 6/2009 |
| EP | 2241280 A2 | 10/2010 |
| JP | 06505906 A | 7/1994 |
| JP | 07250862 A | 10/1995 |
| JP | 2002136599 A | 5/2002 |
| JP | 2002282298 A | 10/2002 |
| JP | 2008523912 A | 7/2008 |
| JP | 2008544809 A | 12/2008 |
| JP | 2010533034 A | 10/2010 |
| JP | 2012521808 A | 9/2012 |
| JP | 2013099549 A | 5/2013 |
| JP | 2013519492 A | 5/2013 |
| JP | 2016512616 A | 4/2016 |
| JP | 2017506562 A | 3/2017 |
| KR | 20150129139 A | 11/2015 |
| WO | 9216259 A1 | 10/1992 |
| WO | 2007054490 A1 | 5/2007 |
| WO | 2008034609 A1 | 3/2008 |
| WO | 2013059564 A1 | 4/2013 |
| WO | 2015130821 | 9/2015 |
| WO | 2015200875 A1 | 12/2015 |

OTHER PUBLICATIONS

Gaasterland et al., "Initial Experience with a New Method of Laser Transscleral Cyclophotocoagulation for Ciliary Ablation in Severy Galucoma", Trans Am Ophthalmol Soc., vol. 90, 1992, pp. 225-246.
Goel et al., "Aqueous Humor Dynamics: A Review", The Open Ophthalmology Journal, vol. 4, Sep. 3, 2010, pp. 52-59.

(56) References Cited

OTHER PUBLICATIONS

Kosoko et al., "Long-Term Outcome of Initial Ciliary Ablation with Contact Diode Laser Transscleral Cyclophotocoagulation for Severe Glaucoma", Ophthalmology, vol. 103, No. 8, Aug. 1996, pp. 1294-1302.

Shields, "Surgical Anatomy", Glaucoma Surgery, Harvard Medical School, Massachusetts Eye and Ear Infirmary, Boston, Massachusetts, Mosby Year Book, 1992, 5 pages.

Tan et al., "Mircopulse Transscleral Diode Laser Cyclophotocoagulation in the Treatment of Refractory Glaucoma", Clinical and Experimental Ophthalmology, vol. 38, No. 3, Apr. 2010, pp. 266-272.

* cited by examiner

HANDHELD OPHTHALMIC LASER SYSTEM WITH REPLACEABLE CONTACT TIPS AND TREATMENT GUIDE

CROSS REFERENCE TO RELATED APPLICATION DATA

The present application is a Continuation of U.S. patent application Ser. No. 16/938,030 filed Jul. 24, 2020 (Allowed); which is a Divisional of U.S. patent application Ser. No. 15/638,036 filed Jun. 29, 2017 (now U.S. Pat. No. 10,758,118); which claims the benefit of U.S. Provisional Appln No. 62/357,012 filed Jun. 30, 2016, the full disclosures which are incorporated herein by reference in their entirety for all purposes.

BACKGROUND OF THE DISCLOSURE

The present disclosure is generally related to medical systems, devices, and methods for treating a glaucomatous eye. In some embodiments, a handheld treatment device is configured for delivering therapeutic light toward a target tissue. The handheld treatment device may be provided with a replaceable distal contact tip. In further embodiments, ophthalmic treatment systems may be provided that include a treatment device for delivering therapeutic light toward a target tissue and a treatment guide for placement against an eye of a patient that may interface with the distal end of the treatment device to align the device with one or more treatment locations about the eye of the patient.

Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Elevated intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, preventing the egress of fluid.

Uveoscleral outflow is a non-conventional pathway that is gaining importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical attempts to lower the production of aqueous humor by the ciliary processes. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, high intensity continuous wave (CW) infrared laser energy is directed through selected portions of the pars plicata region to the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam to a subsurface non-visible target such as the ciliary body can be challenging for a surgeon.

While the prior systems, methods, and devices have provided advancements in the art, further improvements are desired.

SUMMARY OF THE DISCLOSURE

Embodiments of the present disclosure generally relate to ophthalmic laser treatment systems. In some embodiments, the ophthalmic laser treatment systems may include a handheld treatment device having a replaceable distal tip. In further embodiments, the ophthalmic laser treatment system may include a treatment guide configured to cooperate with a handheld treatment device to preferentially align the treatment device with a target tissue of the eye of a patient. In some aspects, the treatment device may be provided to direct therapeutic light toward the ciliary process. For example, in certain embodiments, the treatment device and/or guide may be provided for cyclophotocoagulation of the eye of a patient.

In an embodiment of the disclosure, a handheld glaucoma treatment device for delivering therapeutic light toward a ciliary process of an eye of a patient may be provided. The handheld glaucoma treatment device may include a treatment device housing defining a treatment device handle for grasping by a hand of a user. The housing may have a proximal end and a distal end opposite the proximal end. A therapeutic light source may be housed within the treatment device housing. Optics may also be housed within the treatment device housing and may be configured to direct therapeutic light generated by the therapeutic light source toward the distal end of the treatment device housing. A replaceable contact tip having a proximal end and a distal end may be provided. The proximal end of the replaceable contact tip may be configured to be releaseably coupled with the distal end of the treatment device housing. A contact surface of the distal end of the replaceable contact tip may be configured to couple, contact, and/or engage with a surface of the eye. The replaceable contact tip may be configured to receive therapeutic light generated by the therapeutic light source via the optics housed within the treatment device housing and may be configured to direct the received therapeutic light toward the eye.

Optionally, the treatment device housing may house a power supply configured to power the therapeutic light source. The power supply may be a battery (e.g., single use or rechargeable).

The treatment device housing may define an elongate axis from the proximal end to the distal end of the treatment device housing. The therapeutic light may be projected distally along the elongate axis. The contact surface of the replaceable contact tip may be at a non-ninety degree angle with respect to the elongate axis defined by the treatment device housing (e.g., such that the therapeutic light is directed at a non-normal angle relative to the contact surface of the replaceable contact tip). For example, the contact surface of the replaceable contact tip may be at a 30-60 degree angle with respect to the elongate axis defined by the treatment device housing.

In some embodiments, the contact surface of the replaceable contact tip may be concave to match a curvature of a portion of the eye. For example, in some embodiments, the contact surface may be configured to match a curvature of the sclera of the eye.

In some embodiments, the distal end of the replaceable contact tip may have an alignment edge or feature configured to be aligned with a limbus of the eye.

Optionally, the contact surface of the distal end of the replaceable contact tip may be convex. The replaceable contact tip may include rounded edges so that the distal end of the replaceable contact tip may be swept across the surface of the eye. In certain embodiments, the rounded edges reduce the likelihood that the distal end of the replaceable contact tip catches on the tissue surface of the eye when the treatment device is swept across the surface of the eye.

The replaceable contact tip may include internal optics configured to optically couple with the optics housed within the treatment device housing. For example, the optics of the replaceable contact tip may be an optical fiber having a proximal end and a distal end. The proximal end may optically couple with the optics housed within the treatment device housing when the replaceable contact tip is engaged with the distal end of the treatment device housing. The distal end of the internal optics of the replaceable contact tip may protrude from the contact surface of the replaceable contact tip. For example, the distal end of the optical fiber may protrude from the contact surface of the replaceable contact tip by 1 mm or less (e.g., 0.5 mm as is the case for IRIDEX G-probe).

In other embodiments, the distal end of the optical fiber may protrude from the contact surface of the replaceable contact tip by 2-10 mm or more (e.g., 5 mm).

In some embodiments, the proximal end of the replaceable contact tip couples with the distal end of the treatment device housing through a threaded engagement. Optionally, the proximal end of the replaceable contact tip couples with the distal end of the treatment device housing through a snap-fit engagement.

In still further embodiments, the replaceable contact tip may be configured to map the received therapeutic light generated by the therapeutic light source into a plurality of separate smaller spots so that a plurality of treatment locations may be treated simultaneously.

For example, in certain embodiments, the replaceable contact tip may receive a 1 mm input light and may map the input light with a spot size of 1 mm into a plurality of 10 μm spots or smaller.

Optionally, the replaceable contact tip may be configured to map the received therapeutic light into 2 to 100 spots (e.g., 49 spots in some embodiments).

In some embodiments of the present disclosure, the replaceable contact tip may be one of a plurality of replaceable contact tips. Each of the plurality of replaceable contact tips may be provided for different treatments (e.g., using different therapeutic light parameters) or may have different distal end configurations (e.g., for coupling with different target areas of the eye, for cooperating with a treatment guide, for different methods of therapeutic light delivery, or the like).

For example, the plurality of replaceable contact tips may include a first replaceable contact tip and a second replaceable contact tip. The second replaceable tip may have a proximal end and a distal end. The proximal end of the second replaceable contact tip may be configured to be coupled with the distal end of the treatment device housing. A contact surface of the distal end of the second replaceable contact tip may be configured to engage with the surface of the eye. The distal end of the second replaceable contact tip may have a different configuration than the distal end of the other replaceable contact tip (first replaceable contact tip) and may engage with the eye in a different manner.

In some embodiments, the first replaceable contact tip may have a first computer readable code and the second replaceable contact tip may have a second computer readable code. The treatment device housing may include a device (e.g., scanner) for detecting the first and second computer readable code to determine which of the first and second replaceable contact tips is coupled with the distal end of the treatment device housing. Parameters of the therapeutic light source may be adjusted based on which of the first and second computer readable codes is detected by the scanner.

In further aspects of the present invention, an ophthalmic treatment system may be provided that includes a handheld glaucoma treatment device for delivering therapeutic light toward a ciliary process of an eye of a patient. The handheld glaucoma treatment device may include a treatment device housing defining a treatment device handle for grasping by a hand of a user. The treatment device housing may have a proximal end and a distal end opposite the proximal end. A therapeutic light source may be housed within the treatment device housing. Optics may be housed within the treatment device housing configured to direct therapeutic light generated by the therapeutic light source toward the distal end of the treatment device housing. A replaceable contact tip may be provided, having a proximal end and a distal end. The proximal end of the replaceable contact tip may be configured to be detachably coupled with the distal end of the treatment device housing. The replaceable contact tip may be configured to receive therapeutic light generated by the therapeutic light source via the optics housed within the treatment device housing and may be configured to direct the received therapeutic light toward the eye. The ophthalmic treatment system may further include a treatment guide having a distal surface configured to be placed against a surface of the eye and a proximal surface of the treatment guide being configured to interface with the distal end of the replaceable contact tip to align the replaceable contact tip with one or more treatment locations around the eye.

The replaceable contact tip may include internal optics configured to optically couple with the optics housed within the treatment device housing. The optics of the replaceable contact tip may be an optical fiber having a proximal end optically coupled with the optics housed within the treatment device housing when the replaceable contact tip is coupled with the distal end of the treatment device housing. The optical fiber may have a distal end that protrudes from a contact surface of the distal end of the replaceable contact tip.

The treatment guide may include an aperture extending from the proximal surface to the distal surface. The aperture may be configured to receive the distal end of the optical fiber that protrudes distally from the distal end of the replaceable contact tip and may be configured to align the optical fiber with a target tissue. In some embodiments, the aperture may restrict movement of the optical fiber when the distal end of the optical fiber is received into the aperture.

A thickness of the treatment guide from the distal surface to the proximal surface and a length of the optical fiber that protrudes distally from the distal end of the replaceable contact tip may be dimensioned so that the distal end of the optical fiber protrudes distally from the distal surface of the treatment guide when the optical fiber is received through the aperture of the treatment guide. The thickness of the treatment guide and the length of the optical fiber may be dimensioned so that the distal end of the optical fiber protrudes distally by at least 1 mm from the distal surface of the treatment guide when the optical fiber is received thought the aperture of the treatment guide.

The treatment guide may be a contact ring with a plurality of apertures extending from the proximal surface to the distal surface. The apertures may be radially spaced about the contact ring. In some embodiments, the distal surface of the treatment guide may be curved to conform with the edge contour of the eye (e.g., sclera).

In some embodiments, the replaceable contact tip cooperates with the apertures of the treatment guide to deliver therapeutic light toward a target tissue at an angle not parallel to an optical axis of the eye.

Optionally, the aperture may be a track and the replaceable contact tip may be configured to slidably engage with the track such that the replaceable contact tip can translate along the track while delivering therapeutic light to the target tissue.

The treatment guide may include a perimeter wall configured to engage with an eyelid of the patient and may be configured to maintain the eyelid open during application of the treatment guide against the surface of the eye.

In some embodiments, the treatment guide, the treatment device, or both, may incorporate an illumination light source for transillumination of the eye for the purpose of confirming the location of ciliary bodies or other subsurface ocular structures. In some embodiments, the illumination light source may be coupled with one or more light pipes to facilitate transillumination.

In some aspects, a treatment guide may be provided according to some embodiments of the disclosure. The treatment guide may have an inner edge configured to be aligned with a limbus of the eye. A distal surface of the treatment guide may be configured to be placed against a surface of the eye and a proximal surface being configured to interface with a distal end of a treatment device contact tip to guide the contact tip to one or more treatment locations around the eye.

The treatment guide may include an aperture extending from the proximal surface to the distal surface. The aperture may be configured to receive the distal end of an optical fiber that protrudes distally from the distal end of the contact tip and may be configured to align the optical fiber with a target tissue.

The treatment guide may be a contact ring with a plurality of apertures extending from the proximal surface to the distal surface. The apertures may be radially spaced about the contact ring.

In some embodiments, the contact tip may cooperate with the apertures of the treatment guide to deliver therapeutic light toward a target tissue at an angle not parallel to an optical axis of the eye.

The aperture may be a track and the contact tip may be configured to slidably engage with the track such that the contact tip can translate along the track while delivering therapeutic light to the target tissue.

The track may extend at least 30 degrees about the optical axis of the eye. For example, the track may extend 180 degrees about the optical axis of the eye and in some embodiments, the track may extend at least 270 degrees about the optical axis of the eye.

Optionally, the treatment guide may include a perimeter wall configured to engage with an eyelid of the patient and may be configured to maintain the eyelid open during application of the treatment guide against the surface of the eye.

In still further embodiments, a method for treating an eye of a patient may be provided. The method may include engaging a proximal end of a replaceable contact tip with a distal end of a treatment device housing to optically couple the replaceable contact tip with a therapeutic light source housed within the treatment device housing. A distal end of the replaceable contact tip may be aligned with the ciliary process of the eye. Thereafter the therapeutic light source may be activated to generate therapeutic light and the therapeutic light may be delivered toward the ciliary process of the eye.

In some embodiments, the method may further include applying a treatment guide to the eye. Aligning the distal end of the replaceable contact tip with the ciliary process of the eye may include engaging the distal end of the replaceable contact tip with the treatment guide after the treatment guide is applied to the eye.

In some embodiments, the treatment guide may be a ring and may be positioned over the sclera of the eye of the patient.

In some embodiments, the treatment guide may include a plurality of separate apertures configured to receive a distal end of an optical fiber of the replaceable contact tip therethrough.

Optionally, the replaceable contact tip engages with the apertures of the treatment guide to deliver therapeutic light toward the ciliary process at an angle not parallel to an optical axis of the eye in certain embodiments.

The distal end of the optical fiber of the replaceable contact tip may be configured to protrude from a distal surface of the treatment guide and may indent the surface of the eye.

The treatment guide may include a track in some embodiments. The replaceable contact tip may slidably engage with the track and the replaceable contact tip may be translated along the track during delivery of the therapeutic light to the ciliary process.

In some embodiments, the treatment guide may include a perimeter wall configured to engage with an eyelid of the patient. The perimeter wall of the treatment guide may maintain the eyelid open during application of the treatment guide to the eye.

In some embodiments, the method may include removing a prior contact tip from the treatment device housing prior to engaging the proximal end of the replaceable contact tip with the distal end of the treatment device housing. In some embodiments, the replaceable contact tip may include a computer readable code. The treatment device housing may include a scanner for detecting the first computer readable code. Parameters of the therapeutic light source may be adjusted after detection of the first computer readable code by the scanner.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

BRIEF DESCRIPTION OF THE DRAWINGS

Further details, aspects, and embodiments of the disclosure will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE DISCLOSURE

Ophthalmic laser systems generally require a laser console and a laser probe where the laser console contains the laser source, power supply and controller. The laser probe generally contains an optical fiber and connector for attachment to the laser console. The laser console is typically an AC powered system, placed on a surface that is at least several feet away from a patient's eye, and the laser output light from the console is typically carried by an optical fiber (i.e., waveguide) to the patient's eye where photocoagulation based treatment may take place. Such a system typically requires external AC power, a long multimode fiber to bring light to the end applicator that could be implemented with a slit lamp adapter, a scanner, or a handheld contact probe.

Embodiments of the present invention may provide certain advantages and improvements over standard ophthalmic laser systems. For example, in some embodiments, an ophthalmic laser system may be provided that does not include a traditional laser console. Instead, the treatment device may be configured to house the treatment light source within the device handle. Additionally, in some embodiments, the handheld treatment device may include a user interface, such as dials and buttons, for adjusting various parameters of the therapeutic light. With certain embodiments, the self-contained handheld treatment device may be operated independent of an AC power source. For example, in some embodiments, the handheld treatment device may be battery powered. Additionally, the handheld treatment device may be disposable or may utilize replaceable distal tips in certain embodiments. Many embodiments may be particularly designed for transscleral cyclophotocoagulation where energy is directed through selected portions of the pars plicata region to the ciliary body, structures under the scleral layers, and the overlying conjunctiva to treat a glaucomatous eye.

Figure 1A:
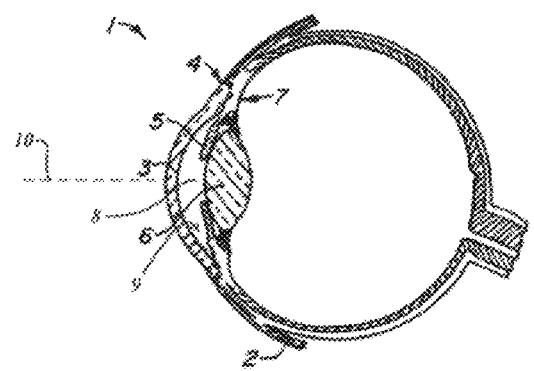
FIG. 1A shows the anatomy of an eye with relevant parts labeled to provide anatomical references.
Figure 1B:
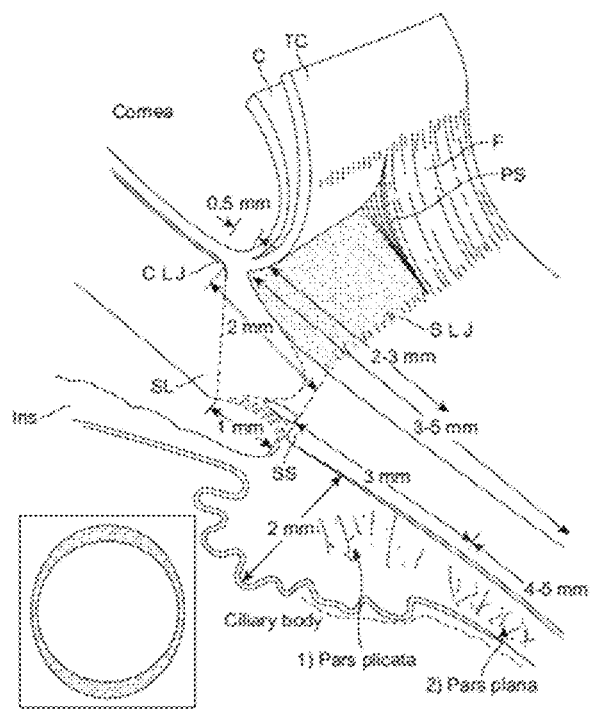
FIG. 1B shows further details of the eye anatomy.

FIGS. 1A-1B illustrate details of the anatomy of an eye. For example, FIG. 1A shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10. FIG. 1B shows further details of the surgical eye anatomy.

Figure 2:
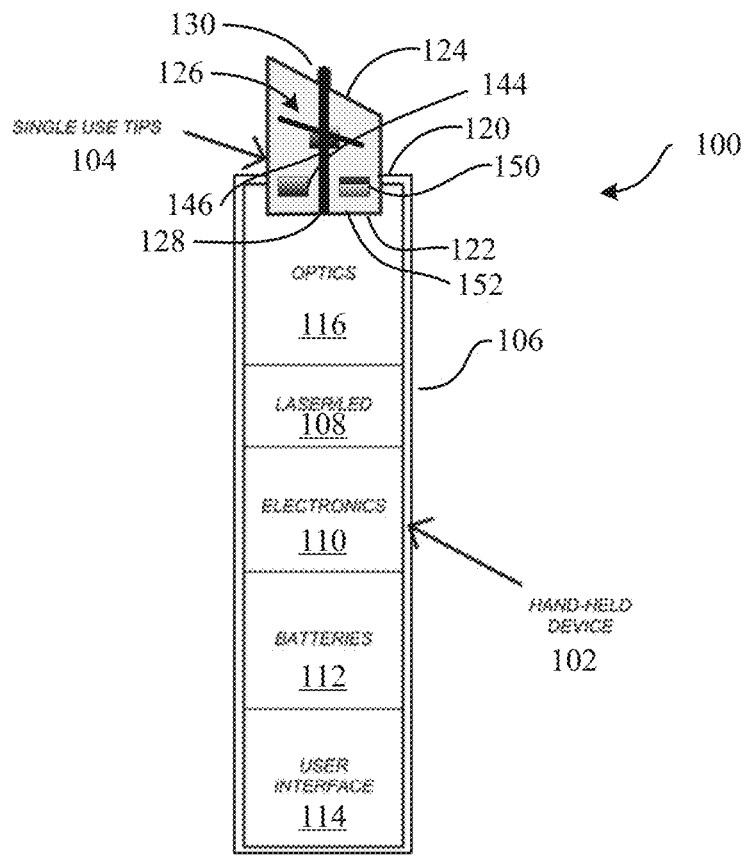
FIG. 2 illustrates an exemplary ophthalmic treatment device according to some embodiments of the disclosure.

Embodiments of treatment devices described herein may target intraocular structures that span from the posterior pars plicata to the pars plana. For example, in some embodiments, the treatment devices may be used to target the ciliary body and/or pars plana. Alternatively, the pars plana may be targeted and the pars plicata, ciliary body, and/or other ciliary processes avoided and vice versa. FIG. 2 illustrates an exemplary ophthalmic treatment device 100 (e.g., probe) according to some embodiments of the disclosure that may be used to target intraocular structures as described above. The ophthalmic treatment device 100 may comprise a treatment device body 102 and a replaceable or single-use tip 104 that is detachably coupled with the treatment device body 102. The treatment device body 102, may include a housing 106 with an exterior surface that defines a handle for grasping by a user. The treatment device body 102 may further include the therapeutic light source 108, associated electronics 110, one or more batteries 112, a user interface 114, and/or internal optics 116.

Figures 3, 4:
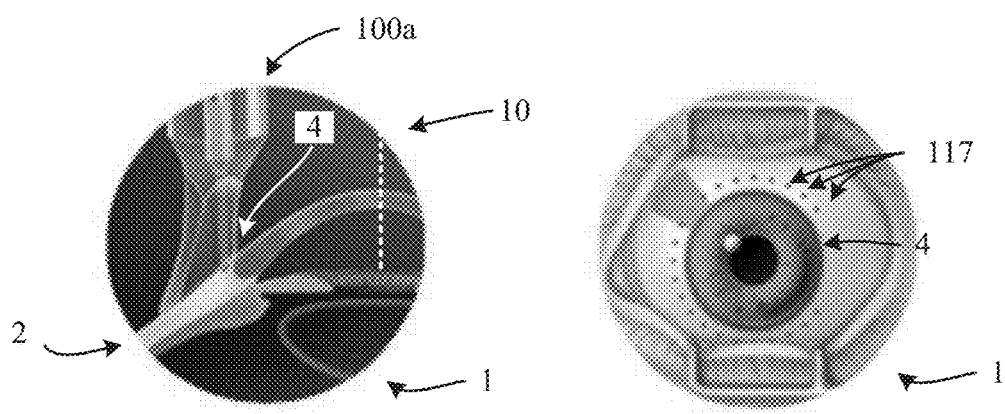
FIG. 3 illustrates an exemplary ophthalmic treatment device aligned with a target tissue according to some embodiments of the disclosure.
FIG. 4 illustrates exemplary treatment spots about the sclera according to some embodiments.

The ophthalmic treatment device 100 may be used to deliver therapeutic light to a target tissue of the eye in a variety of different methods. For example, U.S. Patent Publication 2010/0076419, incorporated herein by reference in its entirety, describes a method of delivering energy toward target tissues at a plurality of spaced apart fixed locations. FIG. 3 illustrates an exemplary placement of an exemplary treatment device 100a with the eye 1 according to some embodiments of the disclosure. The device 100a may be positioned against the sclera 2 and aligned with the limbus 4 of the eye 1. For example, the inner edge of the distal contact end may be aligned with the limbus 4. In some embodiments, the device 100a may be held parallel to the visual axis 10 of the eye 1. The device 100a may then apply energy to a plurality of spaced apart fixed locations 117 about the limbus 4, as illustrated in FIG. 4.

Figure 5:
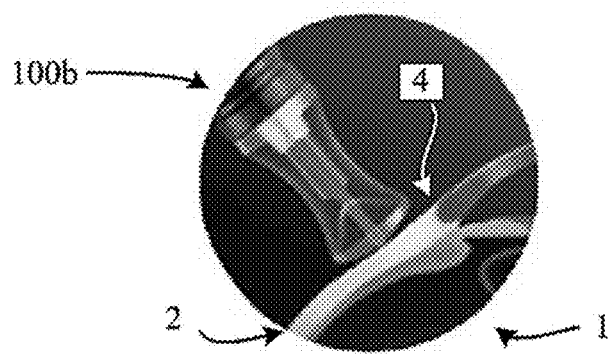
FIG. 5 illustrates another exemplary ophthalmic treatment device aligned with a target tissue according to some embodiments of the disclosure.
Figure 6:
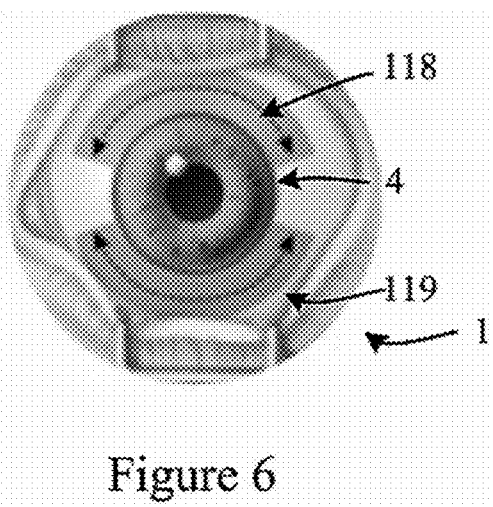
FIG. 6 illustrates exemplary treatment sweeps about the sclera according to some embodiments.

Additionally, U.S. Patent Publication 2015/0374539, incorporated herein by reference in its entirety, describes another treatment method where a treatment device may be slid or swept across the target tissue concurrently with the light delivery. For example, FIG. 5 illustrates an exemplary placement of another exemplary treatment device 100b with the eye 1, according to some embodiments of the disclosure. The device 100b may be positioned against the sclera 2 and aligned with the limbus 4 of the eye 1. In some embodiments, the device 100b may be held at an angle that is not parallel to the visual axis of the eye 1. For example, in some embodiments, the device 100b may be held about perpendicular to the sclera 2. The device 100b may then be slid or swept across the sclera 2 about the limbus 4 during application of the light energy. For example, FIG. 6 illustrates a first sweeping motion 118 from about a 9:30-2:30 clock position, and a separate sweeping motion 119 from about a 3:30-8:30 clock position. While these treatment methods are described in detail, it should be understood they are exemplary and non-limiting. Device placement against and alignment with the eye may be variable and light delivery may vary in other embodiments of the present disclosure.

In some embodiments, the therapeutic light source 108 may be a semi-conductor laser diode or an LED, or the like. In some embodiments, the therapeutic light source 108 may deliver infrared laser energy from a pulsed 810 nm diode laser. In certain embodiments, the therapeutic light source 108 and associated electronics 110 may be configured to deliver light energy in a pulsed or continuous wave emission mode.

Figure 7:
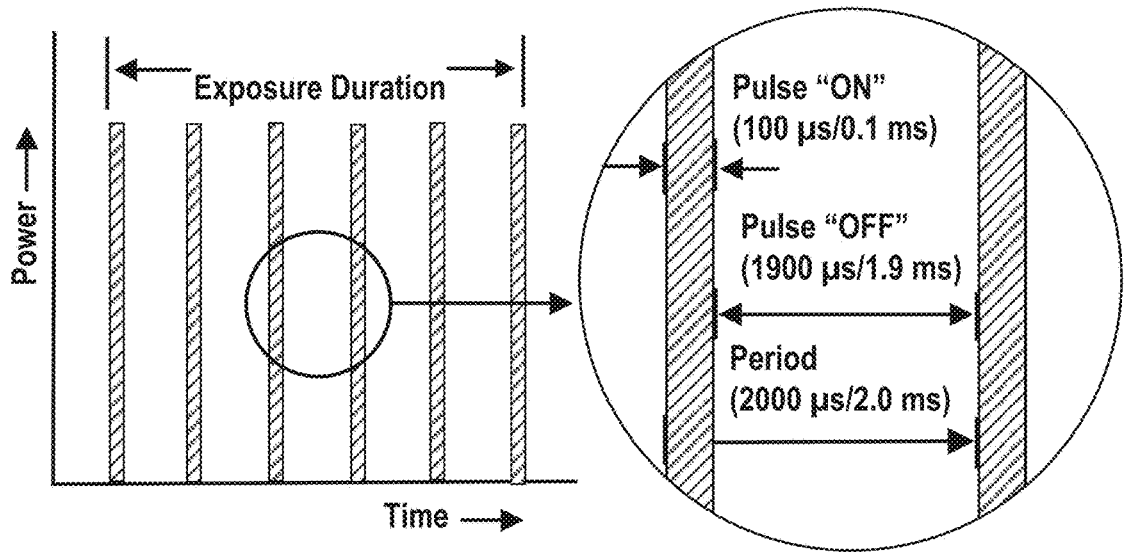
FIG. 7 illustrates exemplary laser parameters for treating an eye according to some embodiments.

For example, in some embodiments, the light source 108 and associated electronics 110 may be configured to operate with a 30% duty cycle, with an "on" time of about 500 µs and an "off" time of about 1100 µs, about a 15% duty cycle, with an "on" time of about 300 µs and an "off" time of about 1700 µs, or about a 10% duty cycle, with an "on" time of about 200 µs and an "off" time of about 1800 µs. Careful selection of the laser energy pulse "on" and "off" times can avoid undesired thermal damage to a target by allowing the target to cool during the "off" time of the laser before the next pulse of energy is delivered during the "on" time. The duty cycle may be selected so that cumulative thermal buildup, caused by insufficient cooling during the "off" time may be avoided. Thus, damage may be reduced to a minimum level sufficient to trigger a biological response needed for lowering of intraocular pressure (IOP). FIG. 7 illustrates an exemplary pulsed mode that may be used in some embodiments of the present invention. The illustrated mode may have an "on" time of 100 µs and an "off" time of 1900 µs with a period of 2000 µs.

In some embodiments where the device is slid across the treatment region of the eye, the treatment laser delivered may comprise pulsed laser energy (e.g., pulsed infrared laser energy). The pulsed laser energy may have a duty cycle between 0.1%-99% and a period of 1 to 5 ms when delivering the laser treatment in a sliding manner. Preferably, the duty cycle may be between 1-5% when delivering the laser treatment in a sliding manner. These ranges may also be advantageous for transscleral treatment delivery.

In some embodiments, the device may incorporate a laser, LED or other optical source capable of directly stimulating a therapeutic response by improving cellular functionality, for example upregulating the biochemical pathways responsible for energy production by mitochondria. A device may incorporate one or more such therapeutic optical sources.

In typical embodiments, a semiconductor laser diode or a semiconductor laser diode pumped laser (e.g., DPSS green/yellow laser) is used as the light source for ophthalmic therapy. Such lasers have defined lasing wavelengths such as 532 nm, 577 nm or 810 nm, and have defined spectral line width such as +/−3 nm, and have defined threshold current such as 700 mA for an 810 nm laser diode, and have defined electrical impedances that allow the lasers to be electrically or optically modulated at any repetition rate (such as 1 kHz or higher), with pulse width at any value (such as 1 ns or higher), for an extended period of time (such as 1 ms or longer).

The light source in the embodiments could be a single mode laser such as a DFB laser, a multimode laser such as an 808 nm broad area laser, or a broad spectrum LED such as a visible spectrum LED for different colors (e.g., green, yellow, or red). The pulse energy, pulse width and pulse repetition rate (aka duty cycle) can be adjusted to provide optimum treatment effect such as demonstrated by the MicroPulse parameters.

Electronics 110 may further include a feedback control implemented in hardware to control the light source 108 power that is faster than the response of a software control loop. The hardware optical power feedback control is preferably implemented with a commercially available laser driver chip that has built-in automatic power control feature that uses photodetector input that correlates with laser output to directly control the bias current of the laser diode to achieve constant power level. This typically results in fast real time power control when compared with a software feedback loop.

In some embodiments, batteries 112 can be an alkaline battery, lead-acid battery, lithium-ion battery, or any other rechargeable or disposable battery. The device body 102 may include a battery receptacle for receiving battery 112 and the housing 106 may include a removable cover for battery 112 replacement when needed, in certain embodiments. The use of a battery 112 to power a therapeutic light source 108 housed in the same housing 16 may allow for more convenient treatments as the device 100 may not need to be tethered to a separate laser console. The lack of tethering to a laser console may also allow for a greater freedom of motion with the device 100 and better targeting of tissues. Additionally, in some embodiments, the battery powered device 100 may allow for the use of the device 100 in rural or secluded areas where electricity is not available. Additionally, embodiments of device 100 housing the light source 108 and the power source 112 may potentially reduce manufacturing costs which may allow for greater availability of device 100 in emerging markets. The batteries could be of rechargeable type and the charging could be done wirelessly.

User interface 114 may comprise one or more mechanical dials, buttons, or switches that may be used to adjust parameters of the therapeutic light source with or without a touchscreen or a dedicated electronic display. The user interface may or may not employ a touch screen display. When a non-touch-screen user interface is employed, simple mechanical display using digits to indicate laser settings could be used. Additionally or alternatively, treatment parameters may be communicated to the device via radio frequency, e.g., Bluetooth.

The housing 106 may further house internal optics 116 that guide the light generated from the light source 108 toward the distal end 120 of housing 106. The terms "proximal" and "distal" are to be taken as relative to the handheld device 100. "Proximal" is to be understood as relatively close to the practitioner holding the device and "distal" is to be understood as relatively farther away from the practitioner holding the device. In some embodiments, the internal optics 116 may include beam shaping optical components such as a collimating lens mechanically and optically coupled with the light source 108. The internal optics may also include any necessary beam shaping elements. Focus and other beam conditioning optics may be separable or integrated with other elements of the light source within the device.

In some embodiments, the housing 106 may optionally include an illumination light source. The illumination light source may be configured to direct light into the eye to illuminate the ciliary process, as described in U.S. Patent Publication 2015/0305938, incorporated by reference herein in its entirety. The illuminated tissue may help a clinician or other practitioner align the device 100 with the tissue during therapeutic light delivery.

The replaceable tip 104 may comprise a proximal end 122 and a distal applicator end 124 opposite the proximal end 122. The replaceable tip 104 may further include optics 126 and, in some embodiments, the replaceable tip 104 may include an optical sensor 144, reflector 146, and/or computer readable media 150 as described in more detail below.

Figure 8:
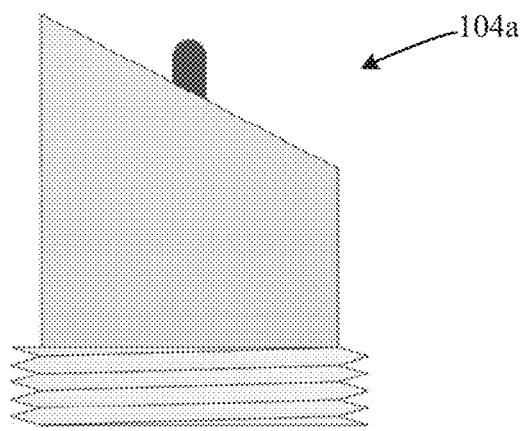
FIG. 8 illustrates an exemplary replaceable contact tip that may be used with ophthalmic treatment devices and systems of the present disclosure according to some embodiments.

The proximal end 122 of the replaceable tip 104 may be configured to mechanically couple with the distal end 120 of the housing 106 of body 102 using one or more engagement features. For example, FIG. 8 illustrates an exemplary replaceable tip 104a, where the proximal end 122 of the replaceable tip 104a has a threaded engagement feature. Accordingly tip 104a may be rotatably engaged and disengaged with the housing 106 of device body 102 having the corresponding threaded engagement feature.

Figure 9A:
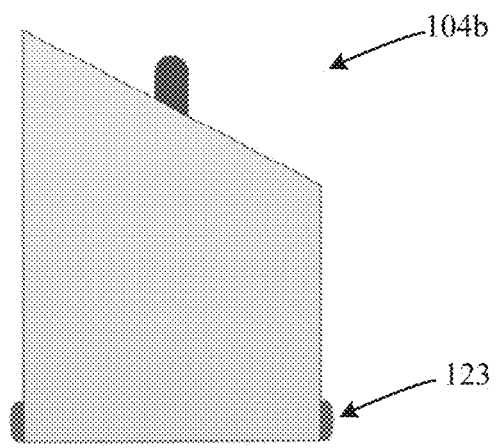
FIG. 9A illustrates another exemplary replaceable contact tip that may be used with ophthalmic treatment devices and systems of the present disclosure according to some embodiments.
Figure 9B:
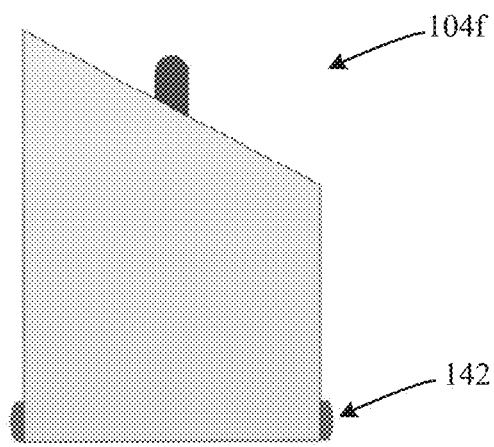
FIG. 9B illustrates another exemplary replaceable contact tip that may be used with ophthalmic treatment devices and systems of the present disclosure according to some embodiments.

FIG. 9A illustrates another exemplary replaceable tip 104b. The exemplary replaceable tip 104b includes a proximal end 122 including one or more protrusions 123 that may snap fit within one or more corresponding engagement features of the device body 102. It should be understood that these illustrated embodiments are exemplary and non-limiting—other variations are possible. For example, in some embodiments, the device body 102 may have a male connector and the replaceable tips 104 may have a female connector or vice-versa. In other embodiments, there may be a length of fiber between the male and female connectors to allow a flexible optical cable between the replaceable tip and the handheld light source. The use of a short optical cable is for, but not limited to, sterilization or other clinical needs. FIG. 9B illustrates yet another exemplary replaceable tip 104f. The exemplary replaceable tip 104f may be magnetically attached to the device body 102 using magnets 142 (e.g., permanent magnets). For example, the tips 104 and the device body 102 can include magnets or be made of or include magnetic material.

Figure 10:
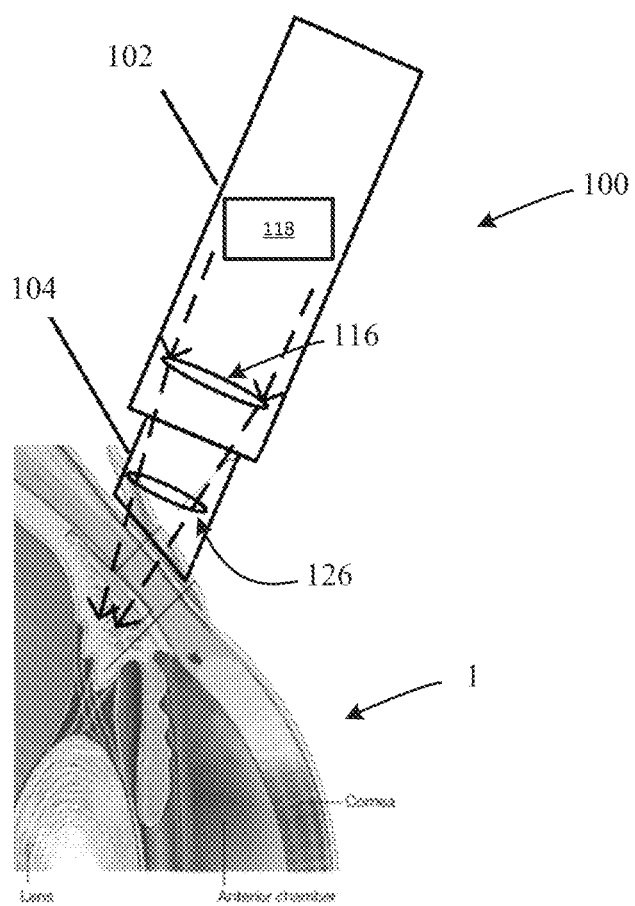
FIG. 10 illustrates the ophthalmic treatment device of FIG. 2 placed against the eye of a patient according to some embodiments.

In some embodiments, a contact surface of the distal end 124 of the replaceable tip 104 may be angled relative to the direction in which therapeutic light is delivered. For example, FIG. 10 illustrates the device 100 of FIG. 2 placed against the eye of a patient. The angled contact surface of distal end 124 may guide the therapeutic light beam into the eye 1 at any preferred angle when the distal end 124 is placed against and aligned with the eye 1. In some embodiments, the distal end 124 may be concave with a curvature configured to match the curvature of the sclera.

The replaceable tip 104 may include optics 126. The optics 126 of replaceable tip 104 may be passive. In some embodiments, the optics 126 may be provided to focus the light into an area under the surface of the eye. Optionally, the optics 126 may diffuse the light into the area under the surface of the eye. In some embodiments, the optics 126 may comprise a multimode fiber having a proximal end 128 and a distal end 130. The proximal end 128 of optics 126 may be configured to optically couple with the optics 116 of device body 102. Additional coupling optics may include any known in the prior art such as any waveguide that connect the ingress and egress ports, and any free-space optical elements that map ingress to the egress port. The refractive index of the material at the distal end 130 of the tip is chosen to match approximately the refractive index of the human tear in the eye to allow high percentage transfer of optical power to target tissue. The distal end 130 of optics 126 may form a blunt tip. In some embodiments, the distal end 130 of optics 126 may be formed by melting back the terminal end of the multimode fiber. As such, in some embodiments, the distal end 130 may be hemispherical in configuration. While optics 126 are illustrated as a multimode fiber, it should be understood that other passive optics may be utilized in other embodiments. For example, the passive optics may comprise any number of lenses, reflectors, refractors, non-imaging optics, and/or imaging optics.

In some embodiments, the tip of distal end 130 may protrude from 0.15 mm to 1.0 mm (e.g., 0.25 mm-4 mm) beyond the contact surface of distal end 124. The protrusion of the tip 130 may increase the transmission of infrared laser energy through the conjunctiva and sclera and may provide beam divergence to irradiate the ciliary body structures from the anterior (pars plicata) through the posterior (pars plana) portions of the ciliary body.

Figure 11:
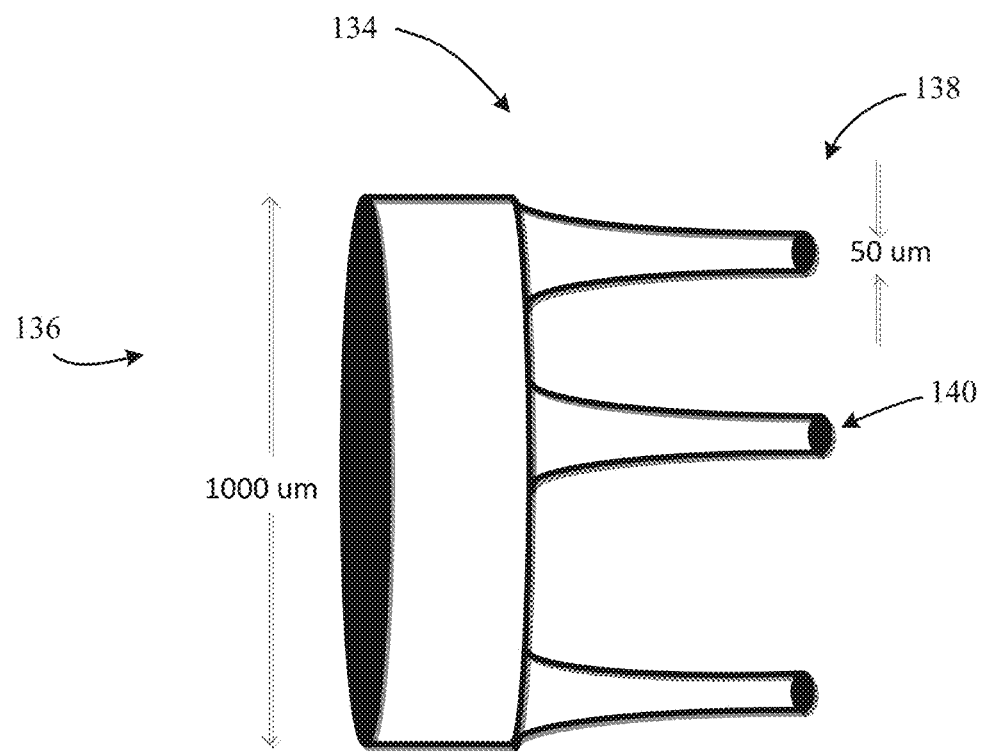
FIG. 11 illustrates an optical element that may be used with certain embodiments of the present disclosure.

In some embodiments, the optics 126 of tip 104 may include an optical element capable of mapping an input light into a plurality of smaller spots. For example, FIG. 11 illustrates an exemplary optical element 134 that may be used with certain embodiments of the present disclosure. The optical element 134 may have a proximal end 136 for receiving an input light and a distal end 138 with a plurality of outputs. The optical element 134 may be configured to map therapeutic light inputted from the proximal end 136 into a plurality of smaller spots 140 at the distal end 138. In some embodiments, the optical element 134 may be a fused glass piece. In certain embodiments, the optical element 134 map a 1000 μm input spot into multiple smaller spots (e.g., 10 μm or the like) spread over a larger area than the 1000 μm input spot. While illustrated as mapping the input light into three smaller spots 140, it should be understood that this is exemplary and non-limiting. Optionally, the optical element 134 may map the input therapeutic light into two or more smaller spots. For example, in some embodiments, it may be beneficial to map an input therapeutic light to 64 or more spots. This may allow multiple locations to be treated with a single input light.

In some embodiments of the disclosure, the replaceable tip 104 may include at least one optical sensor 144 (e.g., a photodiode) that detects reflected or scattered light by eye tissue from therapeutic light directed at the eye tissue during treatment. The reflected or scattered light may be converted into an output signal (e.g., an electrical signal) by the optical sensor 144 and used to assess or calculate incident laser power. The output signal of the optical sensor 144 may be carried across an interface 152 between the tip 104 and device housing 106 by, for example, electrical contacts as described in more detail below. In some embodiments, the output signal or calculated incident laser power can be displayed on the user interface 114. In other embodiments, the replaceable tip 104 can include other types of sensors (e.g., power or pressure).

In certain embodiments of the disclosure, the replaceable tip 104 may include computer readable media 150. The computer readable media 150 may be an optical barcode (e.g., 2D barcode), embedded chip (e.g., encryption, RFID, NFC, direct read memory chip) or the like. The computer readable media 150 may be read by a corresponding sensor or scanner associated with the device body 150. In some embodiments, the computer readable media 150 may be a security feature that protects the device body 102 from being used with unauthorized (e.g., used or counterfeit) replacement tips 104. For example, an encryption or RFID chip may enforce single use of the replaceable tips 104 for each treatment. Optionally, the computer readable media 150 may carry treatment parameter information associated with the replaceable tip 104. For example, a replaceable tip 104 may be coupled with the device body 102. A sensor of the device body or separate sensor (e.g., on an external scanner) may read the computer readable media 150 to determine which treatment parameters are associated with the type of tip 104 that is attached and/or whether the replaceable tip is unauthorized. Thereafter, the electronics 110 of the device body 102 may be configured to automatically adjust parameters of the therapeutic light source 108 for the particular treatment.

In some embodiments, the interface 152 may be a composite optical-electrical interface defined between the tip 104 and device housing 106. The interface can allow optical power and/or electrical signals or circuits (e.g., encryption or RFID chips, antenna matching circuit) to cross between components (e.g., sensors) of the tip 104 and components (e.g., electronics) positioned inside the housing 106. In some embodiments, an optical fiber (e.g., with both optical fibers and electrical wires) may be provided between the tip 104 and housing 106 to allow optical power and/or electrical signals or circuits to cross via the interface. In other embodiments, the optical power and/or electrical signals or circuits can cross the interface 152 via free-space.

In some embodiments of the disclosure, the replaceable tip 104 may include at least one reflector 146. The reflector 146 can direct the laser beam or therapeutic light to a second treatment site at an angle (e.g., perpendicular) relative to light being directed to a first treatment site. For example, in some embodiments, the reflector 146 can direct therapeutic light sideways relative to a longitudinal axis of the tip 104 in a manner known as "side-fire". In this manner, therapeutic light can be directed to treat tumors on an ocular surface of a patient's eye and/or to treat a second site different from the first site. For example, if the first site is the ciliary body in the eye, the second site may be a different intraocular or ocular surface structure. In some embodiments, the optics 126 can include side-fire optical fibers.

Figure 12:
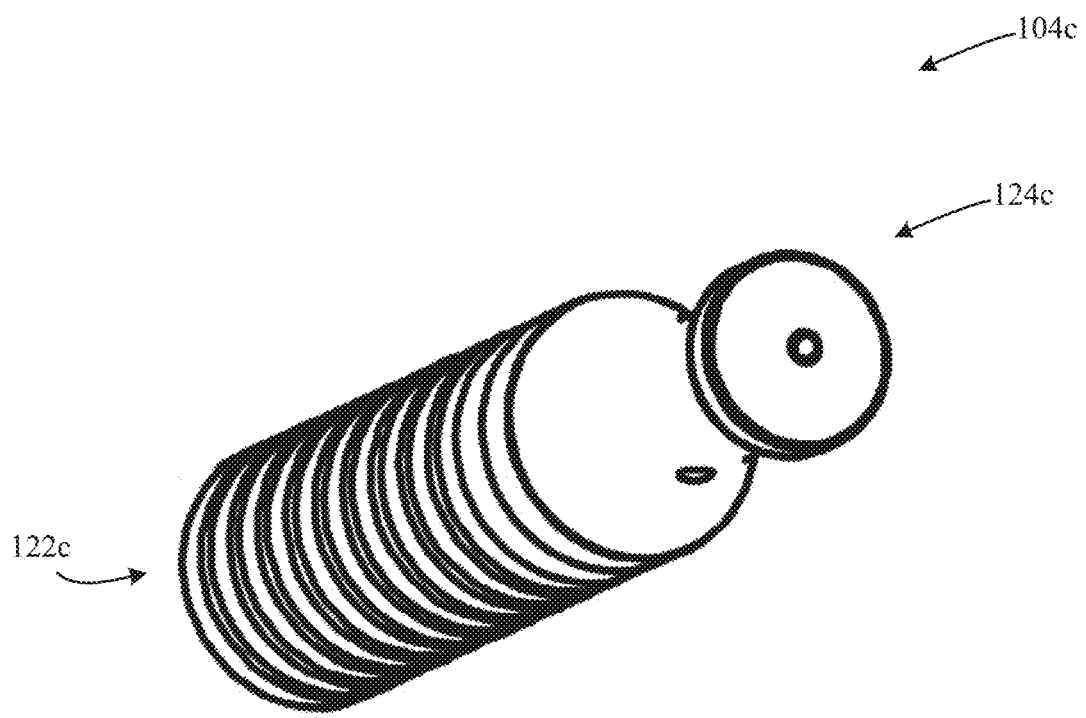
FIG. 12 illustrates another exemplary replaceable contact tip that may be used with ophthalmic treatment devices and systems of the present disclosure according to some embodiments.

While the illustrated distal end 124 of the replaceable tip 104 of device 100 is angled, other configurations may be used in other embodiments of the disclosure. For example, FIG. 12 illustrates an exemplary replaceable tip 104c. Replaceable tip 104c includes a proximal end 122c and a distal end 124c. The proximal end 122c is configured to detachably couple with an associated device body 102. The distal end 124c may be a rounded convex surface that does not match the curvature of the sclera. The rounded convex surface may facilitate sweeping of the device over the sclera during ophthalmic treatment, as described above with reference to FIG. 5 and FIG. 6.

Figure 13:
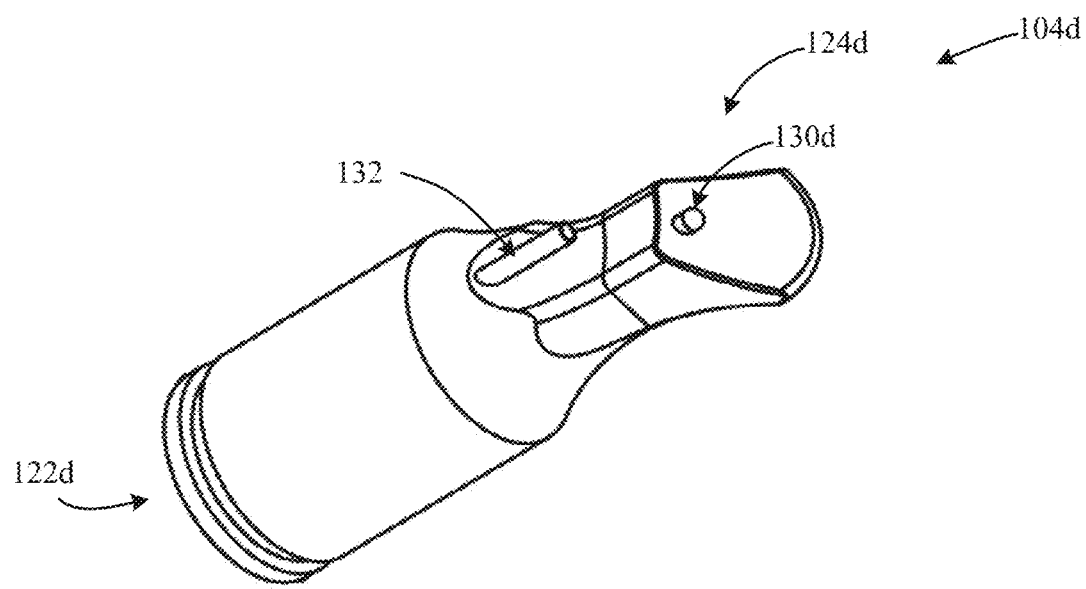
FIG. 13 illustrates another exemplary replaceable contact tip that may be used with ophthalmic treatment devices and systems of the present disclosure according to some embodiments.

FIG. 13 illustrates another exemplary replaceable contact tip 104d that may be used with ophthalmic treatment devices and systems of the present disclosure according to some embodiments. Replaceable contact tip 104d includes an angled and concave distal end 124d that is configured to match the curvature of the sclera. Tip 104d may include an illumination light conduit 132. The illumination light conduit may couple with an illumination light source housed within the housing 106 of device body 102. The conduit 132 may direct the illumination light distally toward the eye to illuminate the ciliary process as described in U.S. Patent Publication 2015/0305938, previously incorporated by reference.

Figure 14:
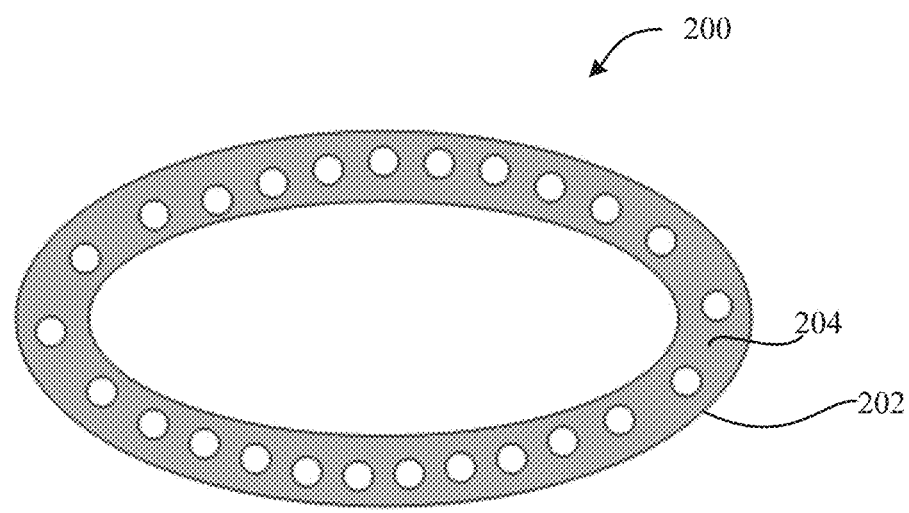
FIG. 14 illustrates top view of an exemplary treatment guide according to some embodiments of the disclosure.
Figure 15:
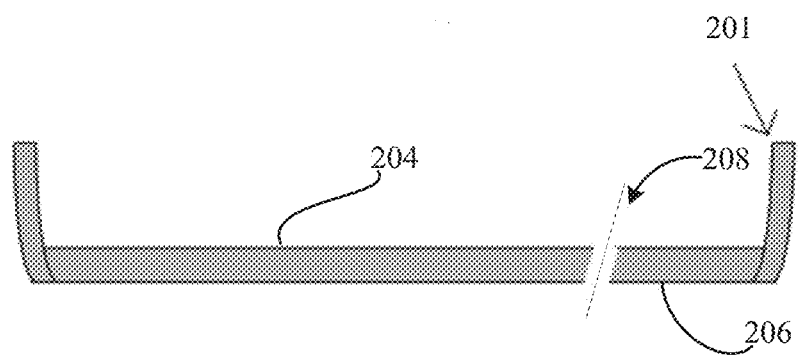
FIG. 15 illustrates a side cross-sectional view of the treatment guide of FIG. 14 according to some embodiments of the disclosure.

Optionally, to further facilitate alignment of a treatment device (e.g., treatment device 100) with the target tissue, a treatment guide may be provided. FIG. 14 illustrates a top view of an exemplary treatment guide 200 according to some embodiments of the disclosure. FIG. 15 illustrates an exemplary side cross-sectional view of the treatment guide 200. The guide may facilitate accurate targeting of a therapeutic light to the various target regions of the eye. Such a guide may help improve consistency and accuracy in various glaucoma treatments since the devices are typically handheld. The guide may comprise an annular guide which engages the eye tissue and guides manual movement of the device to the multiple target regions. Such guides may be registered to and/or mounted on the patient and can provide tactile feedback, and safety elements which inhibit device movement beyond a target tissue. Additionally, the guide may be adjustable so as to be reconfigurable to various eye sizes or to various treatments. In the alternative, the guide may attach to the device and move the device along the guide relative to the tissue.

A treatment guide may include apertures of different sizes in certain embodiments, where each aperture is used for a specifically sized disposable tip. The shape of the contact tip may be a flat surface that is the result of cleaving or polishing, or it may be a round surface that is the result of etching or burning process.

The treatment guide 200 may be a ring 202 in some embodiments. The ring 202 may have a proximal surface 204 and a distal surface 206. The distal surface 206 may be placed against the surface of the eye. For example, in some embodiments, the distal surface 206 may be placed against the sclera and about the cornea of the eye. In some embodiments, an inner edge of the ring 202 may be configured to be aligned with the limbus of the eye. The guide 200 may further include one or more apertures 208 extending from the proximal surface 204 to the distal surface 206. While illustrated as planar, in some embodiments, the distal surface 206 of guide 200 may be concave and configured to match the curvature of the sclera.

Optionally, the treatment guide 200 may include a perimeter wall 201 that extends proximally from the distal surface 206 of the ring 202. The perimeter wall may be configured to keep the eyelids of the patient open during treatment.

The apertures 208 may be positioned about the ring 202 at locations to provide a desired treatment. For example, in some embodiments, the apertures 208 may be between 2.5 mm-3.5 mm from the inner edge of the ring 202 (or a distance optimized for a particular treatment). As illustrated in FIG. 15, the apertures 208 may be at any angle relative to the optical axis of the eye when the guide 200 is aligned and positioned against the eye (for different eyes differently angled designs could be used). The angled apertures 208 may allow the therapeutic light to enter the eye at the desired angle toward the target tissue.

In some embodiments, the apertures may be dimensioned to receive an alignment feature of a corresponding treatment device to preferentially align the treatment device at a desired angle relative to the eye. For instance, in some embodiments, the apertures 208 may be configured to receive the distal end of the multimode fiber of the replaceable tip and to align the multimode fiber at the preferred angle with respect to the surface of the eye. In some embodiments, the apertures 208 may be dimensioned to fit the multimode fiber of the replaceable tip so that the device is limited in translational movement relative to the guide.

Figure 16:
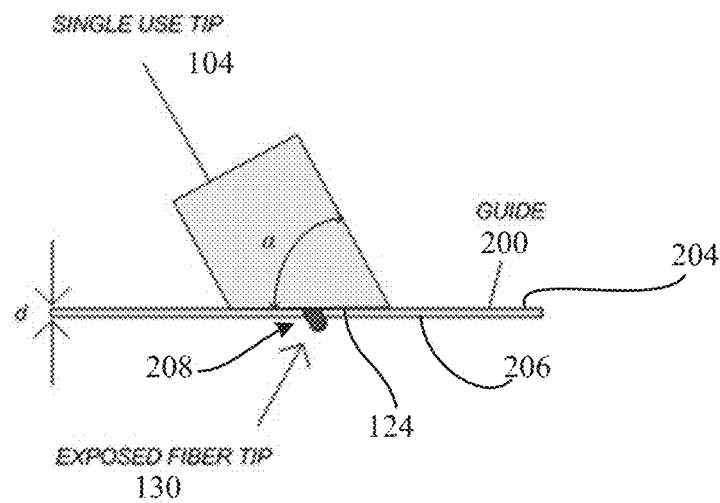
FIG. 16 illustrates an exemplary engagement between a replaceable contact tip and a treatment guide according to some embodiments of the disclosure.

FIG. 16 illustrates an exemplary engagement between a replaceable contact tip 104 of a treatment device and a treatment guide 200 according to some embodiments of the disclosure. As illustrated, in some embodiments, the distal end 130 of the multimode fiber of the contact tip 104 may extend into the aperture 208. In some embodiments, the distal end 130 may extend distally from the distal surface 206 of the treatment guide 200. In some embodiments, the length of the distal end 130 and the thickness d of the treatment guide 200 from the proximal surface 204 to the distal surface 206 may be dimensioned such that the fiber tip 130 extends 0.05 mm-1 mm distally from the distal surface 206 of the treatment guide. For example, if the treatment guide 200 had a thickness d of 2 mm, the fiber tip 130 may extend 2.05 mm-3 mm from the distal surface 124 of the replaceable tip 104. Accordingly, the thickness d of the guide 200 may control a contact pressure of the fiber tip 130 against the surface of the eye. Optionally, in some embodiments, a plurality of treatment guides 200 may be provided that have varying thicknesses such that a clinician can select one that allows the preferred amount of pressure in combination with a replaceable tip 104 for the particular patient.

Figure 17:
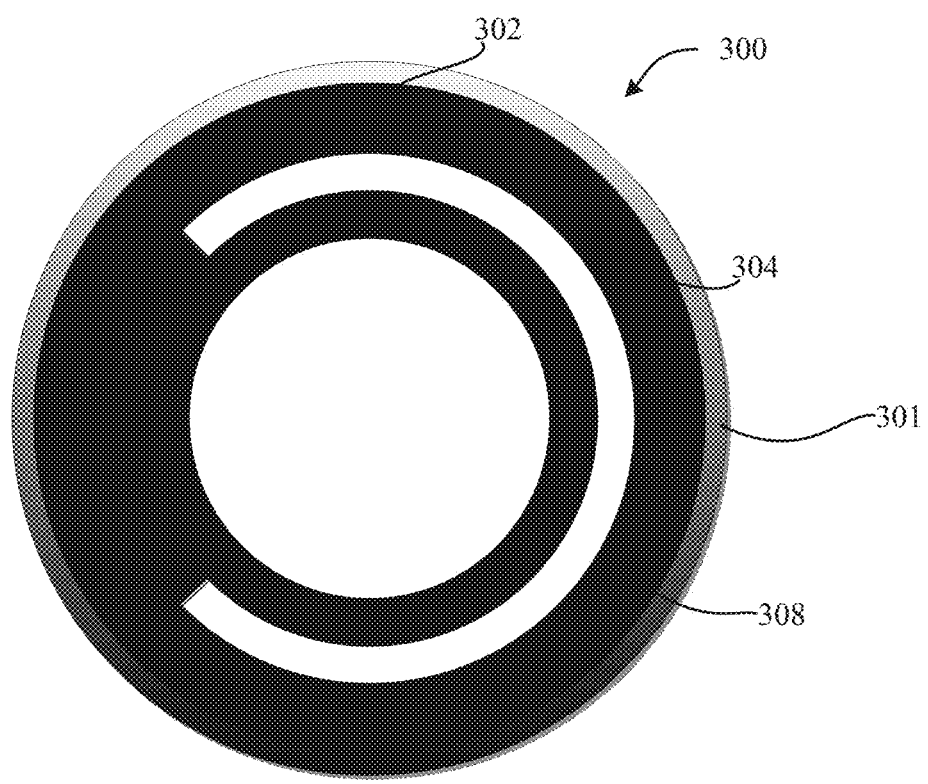
FIG. 17 illustrates another exemplary treatment guide according to some embodiments of the disclosure.

FIG. 17 illustrates a top view of another exemplary treatment guide 300 according to some embodiments of the disclosure. The treatment guide 300 may facilitate device alignment and tissue targeting for a treatment where the treatment device is swept across the eye during therapeutic light delivery.

The treatment guide 300 may be a ring 302 in some embodiments. In certain implementations, an inner edge of ring 302 may be configured to be aligned with a limbus of the eye. Optionally, a perimeter wall 301 may be provided for engaging with the eyelids of a patient to maintain the eyelids open during treatment. The ring 302 may have a proximal surface 304 and a distal surface for engaging a surface of the eye. For example, in some embodiments, the distal surface may be placed against the sclera and about the cornea of the eye and the guide is positioned and fixed at the front of the eye by the force from the eyelids or optionally by the force of the hand with the ring dimensioned appropriately to remain stationery during a treatment session. Optionally, the distal surface of guide 300 may be concave and configured to match the curvature of the sclera. The guide 300 may further include one or more arcuate tracks 308 extending from the proximal surface 304 to the distal surface that is configured to engage with a tip of a laser treatment device and to guide the tip of the laser treatment device along the track 308 during therapeutic light delivery. In some embodiments, the track 308 may be dimensioned to receive the distal end 130 of a replaceable tip 104 into the track 308. Optionally, the distal end 130 of the replaceable tip 104 may protrude distally through the thickness of the guide 308 such that the distal end 130 of the replaceable tip 104 may apply contact pressure against a surface of the eye.

In some embodiments, the track 308 may be spaced about 2.5 mm-3.5 mm from the inner edge of the ring 302. In some embodiments, the track 308 may span 30 degrees-270 degrees of ring 302. Optionally, the track 308, similar to the apertures 208 described above, may be configured to allow therapeutic light to enter at a desired angle into the eye.

In some embodiments, the need for eye stabilization will be eliminated by a handheld laser and its tip-guide since the guide may be lodged inside the eye and may move with the eye. Additionally, the free hand may hold the laser device to stay with the tip/guide so that alignment is always maintained. While guide 200 was described above with single-use replaceable tips 104, it should be understood that the treatment guides described herein may be used with laser devices having replaceable distal tips or may be used with other laser devices such as those described in the references incorporated herein.

In certain embodiments, the treatment guides (e.g., guide 200, guide 300) described herein may be constructed or manufactured by modifying a standard scleral lens. For example, the apertures, tracks, holes or slots of the guides can be formed or made in the scleral lens material to provide a guide with certain features as described herein.

Figure 18:
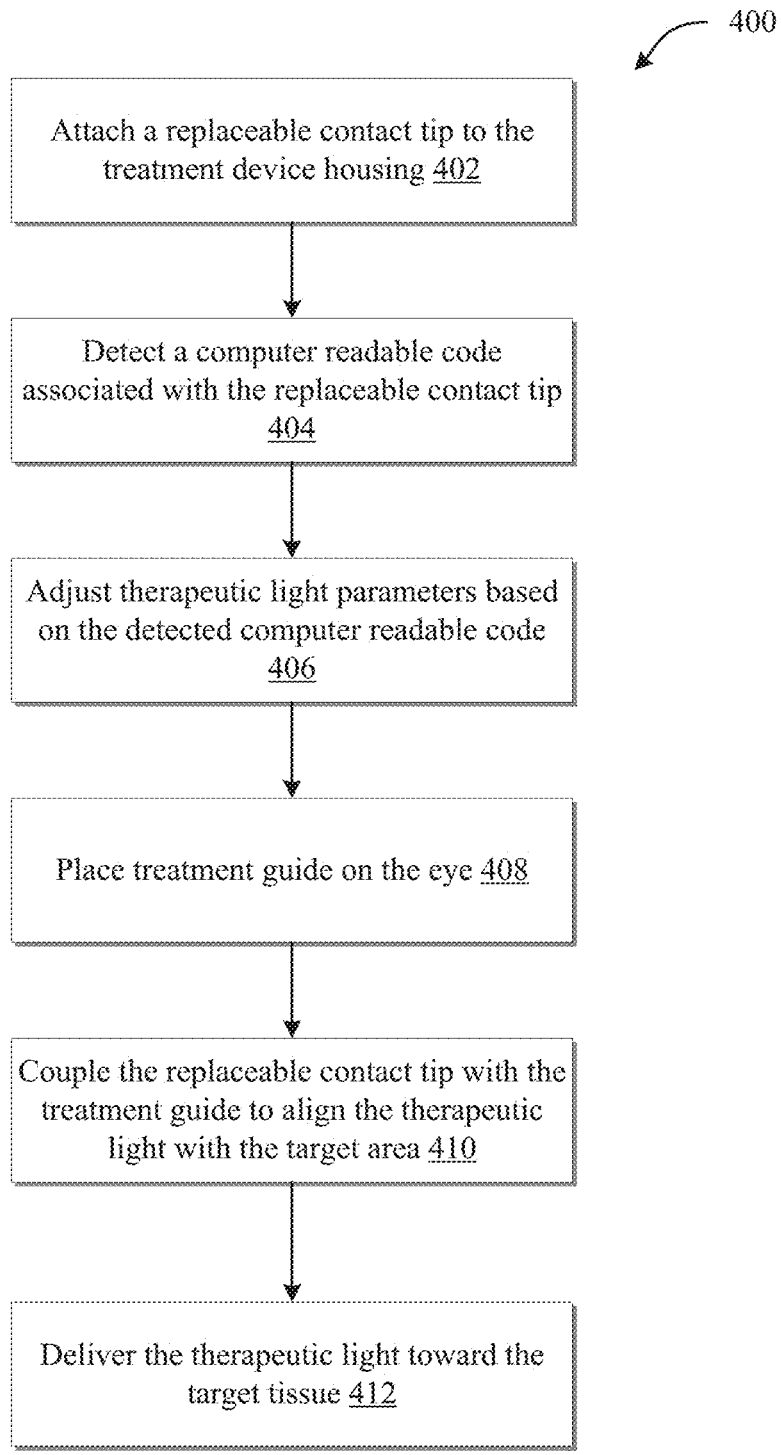
FIG. 18 illustrates an exemplary method of treating an eye according to some embodiments of the disclosure.

In still further embodiments, a method of a treatment of an eye may be provided. FIG. 18 illustrates an exemplary method 400 according to some embodiments of the disclosure. The method 400 may include attaching a replaceable contact tip to the treatment device housing 402. A computer readable code (e.g., code 150) associated with the replaceable contact tip may be detected 404. Therapeutic light parameters may be adjusted based on the detected computer readable code 406. A treatment guide may be placed on the eye 408. Thereafter, the replaceable contact tip may be coupled with the treatment guide to align the therapeutic light with the target tissue 410. After device alignment with the target tissue, the therapeutic light may be delivered toward the target tissue 312.

A replaceable contact tip (e.g., tip 104) may be attached to the treatment device housing (e.g., housing 106 of body 102) in any of the manners described above. For example, the tip may be threadably engaged, snap-fit, or magnetically engaged with a corresponding device body, and/or it is connected to the device housing with a flexible optical fiber (e.g., pigtail optical fiber) that allows flexibility between the device housing and the replaceable tip.

Figure 19:
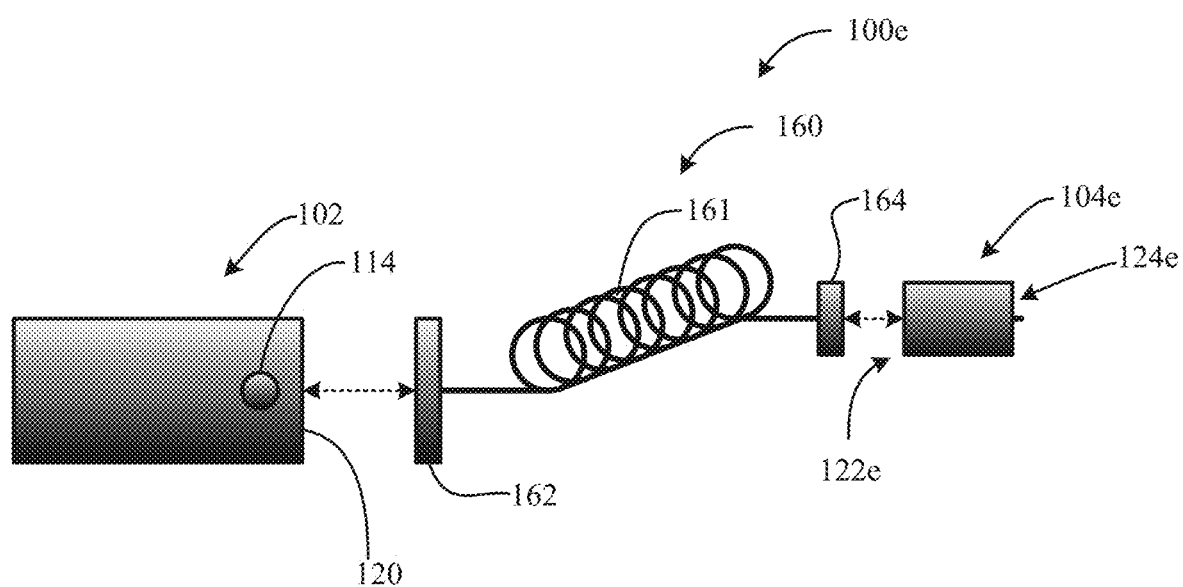
FIG. 19 illustrates an exemplary treatment device with a flexible optical cable coupling a contact tip with a device body, according to some embodiments of the disclosure.

FIG. 19 illustrates an exemplary treatment device 100e having a flexible optical coupler 160 that couples a treatment device body 102 with a replaceable contact tip 104e, according to some embodiments of the disclosure. The treatment device body 102 may be similar to that body illustrated in FIG. 2. The device body 102 may house a therapeutic light source, associated electronics, and a portable power source. Additionally, device body 102 may incorporate the user interface 114. The user interface is illustrated as a simple switch or button that may be depressed to activate the therapeutic light source housed therein to deliver therapeutic light toward the distal end 120 of the body 102. While illustrated as a simple button, the user interface 114 may further include other switches and/or dials for adjusting parameters of the therapeutic light source as described above.

The flexible optical coupler 160 may comprise a flexible optical fiber 161 (e.g., pigtail optical fiber). A proximal end of the flexible optical fiber 161 may be coupled with a proximal connector 162. A distal end of the flexible optical fiber 161 may be coupled with a distal connector 164. The proximal connector 162 may be configured to mechanically couple with the distal end 120 of the device body 102, (threadably, snap-fit, magnetically, or the like). Once the proximal connector 162 is coupled with the distal end 120 of the device body 102, the flexible optical fiber 161 may be optically coupled with the therapeutic light source housed within the device body 102. The distal connector 164 of the flexible optical coupler 160 may be configured to mechanically couple with the proximal end 122e of the replaceable tip 104e (threadably, snap-fit, magnetically or the like). Once the distal connector 164 is coupled with the proximal end 122e of the replaceable tip 104e, the internal optics of the replaceable tip 104e may be optically coupled with the flexible optical fiber 161. With the assembly of the device body 102, the flexible optical coupler 160, and the replaceable tip 104e, activation of the therapeutic light source housed within the device body 102 will be directed from the distal end 124e of the replaceable contact tip 104e.

In some embodiments, the proximal end 122e of replaceable contact tip 104e may have a similar engagement configuration as the proximal connector 162 of flexible optical coupler 160. Similarly, in some embodiments, the distal end 120 of device body 102 may have a similar engagement configuration as the distal connector 164 of flexible optical coupler 160. This may allow the system 100e to be used with or without the flexible optical coupler 160. For example, in certain treatments where the flexible optical coupler 160 is unnecessary, a clinician may directly couple the replaceable tip 104e with the device body 102 given that the proximal end 122e of replaceable tip 104e has a similar engagement configuration as the proximal connector 162 of flexible optical coupler 160, thereby allowing the proximal end 122e of the replaceable tip 104e to couple with the distal end 120 of the device body 102.

In certain embodiments, when electronics are included or embedded in the tip 104e, the optical fiber 161 can act as a composite optical-electrical cable with both an optical fiber and electrical wires to provide an interface between the tip 104e and body 102 for the electrical and optical signals as described above. In such configurations, the connectors 162 and 164 may also support both the optical fiber and electrical wires.

While the replaceable contact tip 104e is illustrated as having a flat distal contact end 124e (perpendicular to the direction of light delivery), it should be understood that replaceable contact tip 104e may have any configuration described above. For example, the replaceable contact tip 104e may be convex (e.g., for sliding treatments), concave (e.g., for mating with the surface of the eye), or angled (e.g., for delivering therapeutic light at a preferred angle relative to the surface of the eye). As set forth above many different replacement tip configurations may be provided for different treatments. Additionally, it should be understood that treatment device 104e may be used with or without a treatment guide (e.g., guide 200, 300 or the like).

The computer readable code may be a barcode, RFID, or other electronic chip or the like, described above. The computer readable code may also act as a security feature that ensures that improper third party treatment tips are not used with the device body 102. Accordingly, in some embodiments, the method may include verifying an authenticity of the replaceable tip coupled with the device body. Optionally, therapeutic light parameters may be adjusted based on the detected computer readable code 406.

The treatment guide may be placed on the eye 408 for the appropriate treatment. For example, if the treatment calls for a plurality of individual treatment spots, a treatment guide like guide 200 may be applied to the eye. On the other hand, if the treatment calls for therapeutic light delivery while the device is swept across a portion of the eye, a treatment guide like guide 300 may be applied to the eye. After placement of the guide on the eye, the replaceable contact tip may be coupled with the treatment guide to align the therapeutic light with the target tissue 410. As set forth above, in some embodiments, a distal end of a multimode fiber of the device tip may be inserted through an aperture or track of the guide to position and align the device tip with the target tissue. Optionally, the distal end of the multimode fiber may protrude distally from the distal surface of the guide to apply pressure to the surface of the eye. After device alignment with the target tissue, the therapeutic light may be delivered toward the target tissue 312.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method for treating glaucoma in an eye of a patient, the method comprising:
    engaging a proximal end of a replaceable contact tip with a distal end of a handheld treatment device housing to optically couple the replaceable contact tip with a therapeutic light source disposed within the treatment device housing;
    aligning a distal end of the replaceable contact tip with the ciliary process of the eye;
    activating the therapeutic light source to generate therapeutic light;
    delivering the therapeutic light with the replaceable contact tip toward the ciliary process of the eye;
    removing a prior contact tip from the treatment device housing prior to engaging the proximal end of the replaceable contact tip with the distal end of the treatment device housing, wherein the replaceable contact tip comprises a first computer readable code, wherein the treatment device housing includes a scanner for detecting the first computer readable code, and wherein parameters of the therapeutic light source are adjusted after detection of the first computer readable code by the scanner, wherein the first computer readable code is stored on a non-transitory computer-readable medium.

2. The method of claim 1, further comprising applying a treatment guide to the eye, and wherein aligning the distal end of the replaceable contact tip with the ciliary process of the eye comprises engaging the distal end of the replaceable contact tip with the treatment guide after the treatment guide is applied to the eye.

3. The method of claim 2, wherein the treatment guide comprises a ring and is positioned over the sclera of the eye of the patient, wherein the treatment guide comprises a plurality of separate apertures configured to receive a distal end of an optical fiber of the replaceable contact tip therethrough.

4. The method of claim 3, wherein the replaceable contact tip engages with the apertures of the treatment guide to deliver therapeutic light toward the ciliary process at an incidence angle to an optical axis of the eye.

5. The method of claim 3, wherein the distal end of the optical fiber of the replaceable contact tip protrudes from a contact surface of the treatment guide and indents the surface of the eye.

6. The method of claim 2, wherein the treatment guide comprises a track and is positioned over the sclera of the eye of the patient, wherein the replaceable contact tip slidably engages with the track and wherein the replaceable contact tip is translated along the track during delivery of the therapeutic light to the ciliary process.

7. The method of claim 2, wherein the treatment guide comprises a perimeter wall configured to engage with an eyelid of the patient, and wherein the perimeter wall of the treatment guide maintains the eyelid open during application of the treatment guide to the eye.

8. The method of claim 1, further comprising selecting between a plurality of alternative replaceable contact tips for engagement with the treatment device, wherein the replaceable contact tips have differing contact surface geometries.

9. The method of claim 1, further comprising selecting between a plurality of alternative treatment guides for engagement with the replaceable contact tip, wherein the treatment guides have differing sizes, apertures, or thicknesses.

10. The method of claim 1, wherein the replaceable contact tip further comprises a reflector and delivering comprises directing a first portion of the therapeutic light toward the eye at a first treatment site and directing a second portion of the therapeutic light toward the eye at a second treatment site.

11. The method of claim 10, wherein the second portion of the therapeutic light is directed at an angle relative to the first portion of the therapeutic light.

12. The method of claim 10, wherein the first portion of the therapeutic light and the second portion of the therapeutic light are directed respectively to the first treatment site and second treatment site concurrently.

13. The method of claim 1, further comprising mapping the therapeutic light generated by the therapeutic light source into a plurality of separate smaller spots with the replaceable contact tip.

14. A handheld glaucoma treatment device for delivering therapeutic light toward an eye of a patient, the handheld glaucoma treatment device comprising:

a treatment device housing defining a handle for grasping by a hand of a user having a proximal end and a distal end opposite the proximal end;

a therapeutic light source disposed within the treatment device housing;

optics disposed within the treatment device housing configured to direct therapeutic light generated by the therapeutic light source toward the distal end of the treatment device housing;

a replaceable contact tip having a proximal end and a distal end, the proximal end of the replaceable contact tip configured to be detachably coupled with the distal end of the treatment device housing and the distal end of the replaceable contact tip comprising a contact surface configured to couple with a surface of the eye, the replaceable contact tip configured to receive therapeutic light generated by the therapeutic light source via the optics housed within the treatment device housing and configured to direct a first portion of the received therapeutic light toward the eye at a first treatment site; and a flexible optical coupler for coupling the proximal end of the replaceable contact tip with the distal end of the treatment device housing, wherein the flexible optical coupler comprises a flexible optical fiber having a proximal end and a distal end, the proximal end of the flexible optical fiber coupled with a proximal connector and the distal end of the flexible optical fiber coupled with a distal connector, and wherein the proximal connector comprises an engagement feature having the same configuration as an engagement feature on a proximal end of the replaceable contact tip, and wherein the distal connector comprises an engagement feature having the same configuration as an engagement feature on a distal end of the treatment device housing.

15. The handheld glaucoma treatment device of claim 14, wherein the replaceable contact tip comprises internal beam forming optics configured to optically couple with the optics housed within the treatment device housing, wherein the optics of the replaceable contact tip comprises an optical fiber having a proximal end optically coupled with the optics housed within the treatment device housing when the replaceable contact tip is coupled with the treatment device housing and a distal end that protrudes from the contact surface of the replaceable contact tip.

16. The handheld glaucoma treatment device of claim 14, wherein the replaceable contact tip further comprises a reflector configured to direct a second portion of the therapeutic light toward the eye at a second treatment site, wherein the second portion of the therapeutic light is directed at an angle relative to the first portion of the therapeutic light.

17. The handheld glaucoma treatment device of claim 14, wherein the replaceable contact tip further comprises a reflector configured to direct a second portion of the therapeutic light toward the eye at a second treatment site, wherein the replaceable contact tip is configured to direct the therapeutic light towards both the first treatment site and second treatment site of the eye concurrently.

18. A handheld glaucoma treatment device for delivering therapeutic light toward an eye of a patient, the handheld glaucoma treatment device comprising:

a treatment device housing defining a handle for grasping by a hand of a user having a proximal end and a distal end opposite the proximal end;

a therapeutic light source disposed within the treatment device housing;

optics disposed within the treatment device housing configured to direct therapeutic light generated by the therapeutic light source toward the distal end of the treatment device housing; and a replaceable contact tip having a proximal end and a distal end, the proximal end of the replaceable contact tip configured to be detachably coupled with the distal end of the treatment device housing and the distal end of the replaceable contact tip comprising a contact surface configured to couple with a surface of the eye, the replaceable contact tip configured to receive therapeutic light generated by the therapeutic light source via the optics housed within the treatment device housing and configured to direct a first portion of the received therapeutic light toward the eye at a first treatment site, wherein the replaceable contact tip defines an elongate axis from the proximal end to the distal end of the replaceable contact tip, wherein the therapeutic light is projected distally along the elongate axis, and wherein the contact surface of the distal end of the replaceable contact tip is at a non-perpendicular angle with respect to the elongate axis defined by the replaceable contact tip, wherein the contact surface of the distal end of the replaceable contact tip is at a 30-60 degree angle with respect to the elongate axis defined by the replaceable contact tip.

* * * * *